United States Patent
Escalante-Semerena et al.

(10) Patent No.: US 6,670,152 B1
(45) Date of Patent: Dec. 30, 2003

(54) ENZYMATIC REDUCTION OF COBALT IN COBALAMIN

(75) Inventors: Jorge C. Escalante-Semerena, Madison, WI (US); Maris V. Fonseca, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/607,003

(22) Filed: Jun. 29, 2000

(51) Int. Cl.$^7$ ................................................ C12P 19/42
(52) U.S. Cl. ......................................................... 435/86
(58) Field of Search ........................................... 435/86

(56) References Cited

PUBLICATIONS

Weickert et al., Optimization of heterologous protein production in *Escherichia coli*. Curr Opin Biotechnol Oct. 1996;7(5):494–9.*

Bianchi et al., "*Escherichia coli* Ferredoxin NADP+ Reductase: Activation of *E. coli* Anaerobic Ribonucleotide Reduction, Cloning of the Gene (fpr), and Overexpression of the Protein," *J. Bacteriology* 175:1590–1595 (1993).

Bianchi, et al., "Flavodoxin is Required for the Activation of the Anaerobic Ribonucleotide Reductase," *Biochemical and Biophysical Reserch Communications* 197:792–797 (1993).

Fujii et al., "Activation of Methionine Synthetase by Reduced Triphosphopyridine Nucleotide–dependent Flavoprotein System," *The Journal of Biological Chemistry* 249:6745–6753 (1974).

Osborne et al., "Isolation, Cloning, Mapping, and Nucleotide Sequencing of the Gene Encoding Flavodoxin in *Escherichia coli*," *Journal of Bacteriology* 173:1729–1737.

O'Toole et al., "Analysis of Mutants of *Salmonella typhimurium* Defective in the Synthesis of the Nucleotide Loop of Cobalamin," *Journal of Bacteriology* 175:3317–3326.

Suh, et al., "Purification and Initial Characterization of the ATP:Corrinoid Adenosyltransferase Encoded by the cobA Gene of *Salmonella typhimurium*," *Journal of Bacteriology* 177:921–925 (1995).

Bauer et al., "Three–Dimensional Structure of ATP:Corrinoid Adenosyltransferase from *Salmonella typhimurium* in Its Free State, Complexed with MgATP, or Complexed with Hydroxycobalamin and MgATP," *Biochemistry* 40:361–374 (2001).

Fonseca et al., "An in Vitro Reducing System for the Enzymic Conversion of Cobalamin to Adenosylcobalmin," *The Journal of Biological Chemistry* 34:32101–32108 (2001).

* cited by examiner

*Primary Examiner*—Ponnathapu Achutamurthy
(74) *Attorney, Agent, or Firm*—Quarles & Brady LLP (57) ABSTRACT

It is disclosed that the enzymes ATP:corrinoid adenosyltransferase (CobA) from *Salmonella typhimurium* and reduced flavodoxin (FldA) from *E. coli* are both necessary and sufficient, in the presence of ATP, to reduce the oxidation state of the cobalt atom in cobalamin and produce adenosylcobalamin. This makes possible the construction of plasmids to confer upon microbial fermentation hosts the ability to synthesize adenosylcobalamin, the supply of which can sometimes be a limitation on microbial growth in fermentation. Since the enzyme flavodoxin reductase (Fpr), also from *E. coli*, can act to reduce FldA for biological activity, that enzyme should preferably be expressed in a fermentation host as well.

6 Claims, 3 Drawing Sheets

A. UV-vis spectrum of authentic AdoCbl. Retention time: 22.9 min.

B. UV-vis spectrum of the reaction product. Retention time: 23.3 min.

FIG 3

SEQUENCE LISTING

<160> NUMBER OF SEQ ID NOS: 6

<210> SEQ ID NO 1
<211> LENGTH: 591
<212> TYPE: DNA
<213> ORGANISM: Salmonella enterica
<220> FEATURE:
<221> NAME/KEY: CDS
<222> LOCATION: (1)..(591)

<400> SEQUENCE: 1

```
atg agt gat gaa cgt tat cag cag cgc cag cag aag gta aaa gat cgg      48
Met Ser Asp Glu Arg Tyr Gln Gln Arg Gln Gln Lys Val Lys Asp Arg
 1               5                  10                  15 gtt gac gcc cgt gtc gcc cag gca cag gaa gag cgc ggt att att atc      96
Val Asp Ala Arg Val Ala Gln Ala Gln Glu Glu Arg Gly Ile Ile Ile
                 20                  25                  30 gtg ttt act ggc aat ggt aag ggc aaa acc acg gcg gct ttc gga act     144
Val Phe Thr Gly Asn Gly Lys Gly Lys Thr Thr Ala Ala Phe Gly Thr
             35                  40                  45 gcc gcc cgc gcc gta gga cac ggt aaa aac gta ggc gtg gtg caa ttt     192
Ala Ala Arg Ala Val Gly His Gly Lys Asn Val Gly Val Val Gln Phe
         50                  55                  60 att aag ggc acc tgg cca aac ggc gag cgt aat ctg ctg gaa ccg cat     240
Ile Lys Gly Thr Trp Pro Asn Gly Glu Arg Asn Leu Leu Glu Pro His
 65                  70                  75                  80 ggc gtc gaa ttt cag gtg atg gca acg gga ttt acc tgg gag acg caa     288
Gly Val Glu Phe Gln Val Met Ala Thr Gly Phe Thr Trp Glu Thr Gln
                 85                  90                  95 aat cgc gag gca gac acc gca gca tgt atg gcc gtt tgg cag cat ggg     336
Asn Arg Glu Ala Asp Thr Ala Ala Cys Met Ala Val Trp Gln His Gly
                100                 105                 110 aaa cgg atg ctg gcc gat ccg ctg ctt gat atg gta gta ctg gat gag     384
Lys Arg Met Leu Ala Asp Pro Leu Leu Asp Met Val Val Leu Asp Glu
            115                 120                 125 ctg acc tat atg gtg gcg tat gac tat tta ccg ctg gaa gag gtc ata     432
Leu Thr Tyr Met Val Ala Tyr Asp Tyr Leu Pro Leu Glu Glu Val Ile
        130                 135                 140 agc gcg cta aac gcg cgc cct ggt cac cag acg gtg att att aca ggt     480
Ser Ala Leu Asn Ala Arg Pro Gly His Gln Thr Val Ile Ile Thr Gly
145                 150                 155                 160 cgc ggc tgt cac cgg gat att ctt gat ctt gcg gat acc gtc agc gaa     528
Arg Gly Cys His Arg Asp Ile Leu Asp Leu Ala Asp Thr Val Ser Glu
                165                 170                 175 ctg cgt ccg gtt aaa cat gct ttt gac gcg ggc gta aaa gcc cag atg     576
Leu Arg Pro Val Lys His Ala Phe Asp Ala Gly Val Lys Ala Gln Met
            180                 185                 190 gga att gat tat taa                                                  591
Gly Ile Asp Tyr
```

-continued

```
            195

<210> SEQ ID NO 2
<211> LENGTH: 196
<212> TYPE: PRT
<213> ORGANISM: Salmonella enterica

<400> SEQUENCE: 2

Met Ser Asp Glu Arg Tyr Gln Gln Arg Gln Gln Lys Val Lys Asp Arg
  1               5                  10                  15

Val Asp Ala Arg Val Ala Gln Ala Gln Glu Glu Arg Gly Ile Ile Ile
             20                  25                  30

Val Phe Thr Gly Asn Gly Lys Gly Lys Thr Thr Ala Ala Phe Gly Thr
         35                  40                  45

Ala Ala Arg Ala Val Gly His Gly Lys Asn Val Gly Val Val Gln Phe
     50                  55                  60

Ile Lys Gly Thr Trp Pro Asn Gly Glu Arg Asn Leu Leu Glu Pro His
 65                  70                  75                  80

Gly Val Glu Phe Gln Val Met Ala Thr Gly Phe Thr Trp Glu Thr Gln
                 85                  90                  95

Asn Arg Glu Ala Asp Thr Ala Ala Cys Met Ala Val Trp Gln His Gly
            100                 105                 110

Lys Arg Met Leu Ala Asp Pro Leu Leu Asp Met Val Val Leu Asp Glu
        115                 120                 125

Leu Thr Tyr Met Val Ala Tyr Asp Tyr Leu Pro Leu Glu Glu Val Ile
    130                 135                 140

Ser Ala Leu Asn Ala Arg Pro Gly His Gln Thr Val Ile Ile Thr Gly
145                 150                 155                 160

Arg Gly Cys His Arg Asp Ile Leu Asp Leu Ala Asp Thr Val Ser Glu
                165                 170                 175

Leu Arg Pro Val Lys His Ala Phe Asp Ala Gly Val Lys Ala Gln Met
            180                 185                 190

Gly Ile Asp Tyr
            195

<210> SEQ ID NO 3
<211> LENGTH: 531
<212> TYPE: DNA
<213> ORGANISM: Escherichia coli
<220> FEATURE:
<221> NAME/KEY: CDS
<222> LOCATION: (1)..(531)

<400> SEQUENCE: 3 atg gct atc act ggc atc ttt ttc ggc agc gac acc ggt aat acc gaa    48
Met Ala Ile Thr Gly Ile Phe Phe Gly Ser Asp Thr Gly Asn Thr Glu
  1               5                  10                  15 aat atc gca aaa atg att caa aaa cag ctt ggt aaa gac gtt gcc gat    96
Asn Ile Ala Lys Met Ile Gln Lys Gln Leu Gly Lys Asp Val Ala Asp
             20                  25                  30 gtc cat gac att gca aaa agc agc aaa gaa gat ctg gaa gct tat gac   144
Val His Asp Ile Ala Lys Ser Ser Lys Glu Asp Leu Glu Ala Tyr Asp
         35                  40                  45 att ctg ctg ctg ggc atc cca acc tgg tat tac ggc gaa gcg cag tgt   192
Ile Leu Leu Leu Gly Ile Pro Thr Trp Tyr Tyr Gly Glu Ala Gln Cys
     50                  55                  60 gac tgg gat gac ttc ttc ccg act ctc gaa gag att gat ttc aac ggc   240
Asp Trp Asp Asp Phe Phe Pro Thr Leu Glu Glu Ile Asp Phe Asn Gly
 65                  70                  75                  80
```

-continued

```
aaa ctg gtt gcg ctg ttt ggt tgt ggt gac cag gaa gat tac gcc gaa      288
Lys Leu Val Ala Leu Phe Gly Cys Gly Asp Gln Glu Asp Tyr Ala Glu
                85                  90                  95 tat ttc tgc gac gca ttg ggc acc atc cgc gac atc att gaa ccg cgc      336
Tyr Phe Cys Asp Ala Leu Gly Thr Ile Arg Asp Ile Ile Glu Pro Arg
            100                 105                 110 ggt gca acc atc gtt ggt cac tgg cca act gcg ggc tat cat ttc gaa      384
Gly Ala Thr Ile Val Gly His Trp Pro Thr Ala Gly Tyr His Phe Glu
        115                 120                 125 gca tca aaa ggt ctg gca gat gac gac cac ttt gtc ggt ctg gct atc      432
Ala Ser Lys Gly Leu Ala Asp Asp Asp His Phe Val Gly Leu Ala Ile
    130                 135                 140 gac gaa gac cgt cag ccg gaa ctg acc gct gaa cgt gta gaa aaa tgg      480
Asp Glu Asp Arg Gln Pro Glu Leu Thr Ala Glu Arg Val Glu Lys Trp
145                 150                 155                 160 gtt aaa cag att tct gaa gag ttg cat ctc gac gaa att ctc aat gcc      528
Val Lys Gln Ile Ser Glu Glu Leu His Leu Asp Glu Ile Leu Asn Ala
                165                 170                 175 tga                                                                   531
```

<210> SEQ ID NO 4
<211> LENGTH: 176
<212> TYPE: PRT
<213> ORGANISM: Escherichia coli

<400> SEQUENCE: 4

```
Met Ala Ile Thr Gly Ile Phe Phe Gly Ser Asp Thr Gly Asn Thr Glu
  1               5                  10                  15

Asn Ile Ala Lys Met Ile Gln Lys Gln Leu Gly Lys Asp Val Ala Asp
                20                  25                  30

Val His Asp Ile Ala Lys Ser Ser Lys Glu Asp Leu Glu Ala Tyr Asp
            35                  40                  45

Ile Leu Leu Leu Gly Ile Pro Thr Trp Tyr Tyr Gly Glu Ala Gln Cys
        50                  55                  60

Asp Trp Asp Asp Phe Phe Pro Thr Leu Glu Glu Ile Asp Phe Asn Gly
 65                  70                  75                  80

Lys Leu Val Ala Leu Phe Gly Cys Gly Asp Gln Glu Asp Tyr Ala Glu
                85                  90                  95

Tyr Phe Cys Asp Ala Leu Gly Thr Ile Arg Asp Ile Ile Glu Pro Arg
            100                 105                 110

Gly Ala Thr Ile Val Gly His Trp Pro Thr Ala Gly Tyr His Phe Glu
        115                 120                 125

Ala Ser Lys Gly Leu Ala Asp Asp Asp His Phe Val Gly Leu Ala Ile
    130                 135                 140

Asp Glu Asp Arg Gln Pro Glu Leu Thr Ala Glu Arg Val Glu Lys Trp
145                 150                 155                 160

Val Lys Gln Ile Ser Glu Glu Leu His Leu Asp Glu Ile Leu Asn Ala
                165                 170                 175
```

<210> SEQ ID NO 5
<211> LENGTH: 747
<212> TYPE: DNA
<213> ORGANISM: Escherichia coli
<220> FEATURE:
<221> NAME/KEY: CDS
<222> LOCATION: (1)..(747)

<400> SEQUENCE: 5

-continued

```
atg gct gat tgg gta aca ggc aaa gtc act aaa gtg cag aac tgg acc      48
Met Ala Asp Trp Val Thr Gly Lys Val Thr Lys Val Gln Asn Trp Thr
  1               5                  10                  15 gac gcc ctg ttt agt ctc acc gtt cac gcc ccc gtg ctt ccg ttt acc      96
Asp Ala Leu Phe Ser Leu Thr Val His Ala Pro Val Leu Pro Phe Thr
             20                  25                  30 gcc ggg caa ttt acc aag ctt ggc ctt gaa atc gac ggc gaa cgc gtc     144
Ala Gly Gln Phe Thr Lys Leu Gly Leu Glu Ile Asp Gly Glu Arg Val
         35                  40                  45 cag cgc gcc tac tcc tat gta aac tcg ccc gat aat ccc gat ctg gag     192
Gln Arg Ala Tyr Ser Tyr Val Asn Ser Pro Asp Asn Pro Asp Leu Glu
 50                  55                  60 ttt tac ctg gtc acc gtc ccc gat ggc aaa tta agc cca cga ctg gcg     240
Phe Tyr Leu Val Thr Val Pro Asp Gly Lys Leu Ser Pro Arg Leu Ala
 65                  70                  75                  80 gca ctg aaa cca ggc gat gaa gtg cag gtg gtt agc gaa gcg gca gga     288
Ala Leu Lys Pro Gly Asp Glu Val Gln Val Val Ser Glu Ala Ala Gly
                 85                  90                  95 ttc ttt gtg ctc gat gaa gtg ccg cac tgc gaa acg cta tgg atg ctg     336
Phe Phe Val Leu Asp Glu Val Pro His Cys Glu Thr Leu Trp Met Leu
            100                 105                 110 gca acc ggt aca gcg att ggc cct tat tta tcg att ctg caa cta ggt     384
Ala Thr Gly Thr Ala Ile Gly Pro Tyr Leu Ser Ile Leu Gln Leu Gly
        115                 120                 125 aaa gat tta gat cgc ttc aaa aat ctg gtc ctg gtg cac gcc gca cgt     432
Lys Asp Leu Asp Arg Phe Lys Asn Leu Val Leu Val His Ala Ala Arg
    130                 135                 140 tat gcc gcc gac tta agc tat ttg cca ctg atg cag gaa ctg gaa aaa     480
Tyr Ala Ala Asp Leu Ser Tyr Leu Pro Leu Met Gln Glu Leu Glu Lys
145                 150                 155                 160 cgc tac gaa gga aaa ctg cgc att cag acg gtg gtc agt cgg gaa acg     528
Arg Tyr Glu Gly Lys Leu Arg Ile Gln Thr Val Val Ser Arg Glu Thr
                165                 170                 175 gca gcg ggg tcg ctc acc gga cgg ata ccg gca tta att gaa agt ggg     576
Ala Ala Gly Ser Leu Thr Gly Arg Ile Pro Ala Leu Ile Glu Ser Gly
            180                 185                 190 gaa ctg gaa agc acg att ggc ctg ccg atg aat aaa gaa acc agc cat     624
Glu Leu Glu Ser Thr Ile Gly Leu Pro Met Asn Lys Glu Thr Ser His
        195                 200                 205 gtg atg ctg tgc ggc aat cca cag atg gtg cgc gat aca caa cag ttg     672
Val Met Leu Cys Gly Asn Pro Gln Met Val Arg Asp Thr Gln Gln Leu
    210                 215                 220 ctg aaa gag acc cgg cag atg acg aaa cat tta cgt cgc cga ccg ggc     720
Leu Lys Glu Thr Arg Gln Met Thr Lys His Leu Arg Arg Pro Gly
225                 230                 235                 240 cat atg aca gcg gag cat tac tgg taa                                  747
His Met Thr Ala Glu His Tyr Trp
                245
```

<210> SEQ ID NO 6
<211> LENGTH: 248
<212> TYPE: PRT
<213> ORGANISM: Escherichia coli

<400> SEQUENCE: 6

```
Met Ala Asp Trp Val Thr Gly Lys Val Thr Lys Val Gln Asn Trp Thr
  1               5                  10                  15

Asp Ala Leu Phe Ser Leu Thr Val His Ala Pro Val Leu Pro Phe Thr
             20                  25                  30

Ala Gly Gln Phe Thr Lys Leu Gly Leu Glu Ile Asp Gly Glu Arg Val
```

-continued

```
                   35                  40                  45
Gln Arg Ala Tyr Ser Tyr Val Asn Ser Pro Asp Asn Pro Asp Leu Glu
        50                  55                  60
Phe Tyr Leu Val Thr Val Pro Asp Gly Lys Leu Ser Pro Arg Leu Ala
 65                  70                  75                  80
Ala Leu Lys Pro Gly Asp Glu Val Gln Val Val Ser Glu Ala Ala Gly
                85                  90                  95
Phe Phe Val Leu Asp Glu Val Pro His Cys Glu Thr Leu Trp Met Leu
                100                 105                 110
Ala Thr Gly Thr Ala Ile Gly Pro Tyr Leu Ser Ile Leu Gln Leu Gly
            115                 120                 125
Lys Asp Leu Asp Arg Phe Lys Asn Leu Val Leu Val His Ala Ala Arg
    130                 135                 140
Tyr Ala Ala Asp Leu Ser Tyr Leu Pro Leu Met Gln Glu Leu Glu Lys
145                 150                 155                 160
Arg Tyr Glu Gly Lys Leu Arg Ile Gln Thr Val Val Ser Arg Glu Thr
                165                 170                 175
Ala Ala Gly Ser Leu Thr Gly Arg Ile Pro Ala Leu Ile Glu Ser Gly
            180                 185                 190
Glu Leu Glu Ser Thr Ile Gly Leu Pro Met Asn Lys Glu Thr Ser His
        195                 200                 205
Val Met Leu Cys Gly Asn Pro Gln Met Val Arg Asp Thr Gln Gln Leu
    210                 215                 220
Leu Lys Glu Thr Arg Gln Met Thr Lys His Leu Arg Arg Arg Pro Gly
225                 230                 235                 240
His Met Thr Ala Glu His Tyr Trp
                245
```

ENZYMATIC REDUCTION OF COBALT IN COBALAMIN

STATEMENT REGARDING FEDERALLY SPONSORED RESEARCH OR DEVELOPMENT

This invention was made with United States government support awarded by the following agencies: NIH GM40313. The United States has certain rights in this invention.

BACKGROUND OF THE INVENTION

Figure 1:
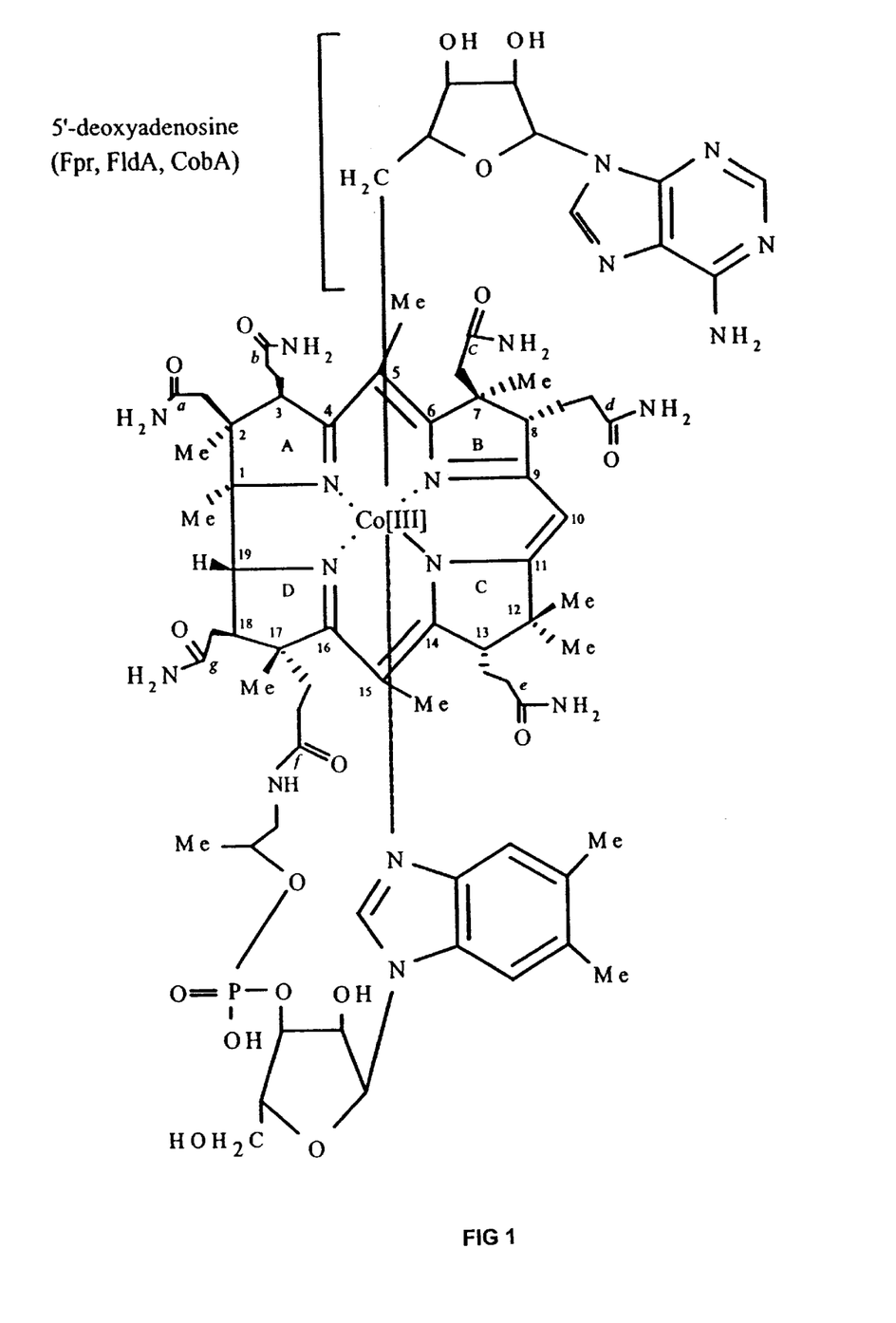
FIG. 1 illustrates the chemical structure of adenosylcobalamin.

Cobabalamin is an essential nutrient to most organisms, including humans. Structurally, cobalamin is an elaborate molecule composed of a cobalt-containing macrocyclic tetrapyrrole, the corrin ring, a nucleotide loop whose base serves as a lower ligand to the cobalt, and an aminopropanol moiety that joins the nucleotide loop to the corrin macrocycle. The structure of cobalamin is shown in FIG. 1. Cobalamin molecules may contain different chemical groups as upper ligands to the cobalt in the corrin ring (e.g. —OH, —$H_2O$, —CN, —$CH_3$ and adenosyl).

Cyanocobalamin, also known as vitamin B12, is a form of cobalamin that contains a cyano (CN) group as an upper ligand. This is the form of cobalamin that is made and sold commercially and is also available as a chemical reagent on the commercial market. The biologically active form of cobalamin contains an adenosyl (Ado) group as the upper ligand to the cobalt. Non-biologically active forms of cobalamin, such as vitamin B 12, must therefore be converted to adenosylcobalamin for use by living organisms. Conversion from cyanocobalamin to adenosylcobalamin requires the reduction of the cobalt atom from Co[III] to the Co[I] oxidation state as well as the transfer of the adenosyl moiety of ATP to the Co[I] form of cobalamin. The enzyme that catalyzes the transfer of the adenosyl group to the corrin ring, an ATP:corrinoid adenosyltransferase (CobA), has been identified and characterized in several organisms in which this process has been studied. In order for adenosyltransferase to function, the cobalt atom must be in the Co[I] oxidation state, but this enzyme is not capable of reducing the oxidation state of the cobalt molecule in cobalamin.

Biological production of chemicals with industrial value has been greatly improved by the use of large scale bacterial cultures employing genetically engineered strains. The efficient operation of several of such bacterial production processes requires the addition of exogenous adenosylcobalamin to the culture medium. While adenosylcobalamin can be added to such a culture, it is a relatively expensive constituent that can raise the cost of the overall process. In addition, the inability of the bacterial culture to recycle adenosylcobalamin can lead to significantly lower yields of the desired product. This raises the need for a system in which bacterial hosts can be engineered to generate and recycle adenosylcobalamin to make the overall production process more cost-effective and increasing yields.

BRIEF SUMMARY OF THE INVENTION

It is first disclosed here that a combination of the enzymes ATP:corrinoid adenosyltransferase (CobA) and flavodoxin (FldA) are both necessary and sufficient for a bacteria in fermentation culture to produce adenosylcobalamin from cyanocobalamin. By also adding the enzyme flavodoxin (ferrodoxin):NADP+ reductase (Fpr), the FldA can be recycled so that the adenosylcobalamin can be recycled continuously during a fermentation process.

It is also taught here that bacterial expression vectors can be constructed containing genes encoding the expression of both CobA and FldA in bacterial hosts. The transformation of such expression vectors into a fermentation host confers upon that host the ability to produce adenosylcobalamin from cyanocobalamin, thereby lowering the fermentation costs for that bacteria. The expression vector can also carry a construct encoding the expression of Fpr.

It is an advantageous variant of the present invention that genes encoding all three enzymes, CobA, FldA and Fpr, can be combined on a single plasmid to make a plasmid that, when transferred into a bacterial host, makes that host independent of the need for external adenosylcobalamin in fermentation culture.

Other objects advantages and features of the present specification will become apparent from the following specification.

DETAILED DESCRIPTION OF THE INVENTION

The specific components of an enzymic system that is capable of generating adenosylcobalamin from non-adenosylated cobalamin are described here for the first time. The enzymes ATP:corrinoid adenosyltransferase (CobA) and reduced flavodoxin (FldA) acting together can produce adenosylcobalamin from cyanocobalamin, reducing cobalt in the process. In this system, the enzyme flavodoxin (ferrodoxin):NADP+ reductase (Fpr) reduces the FldA enzyme. Reduced FldA will interact with CobA to generate cobalamin with the cobalt in the Co[I] state for adenosylation by CobA.

Neither CobA alone nor reduced flavodoxin alone are capable of catalyzing the desired reactions.

Figure 2:
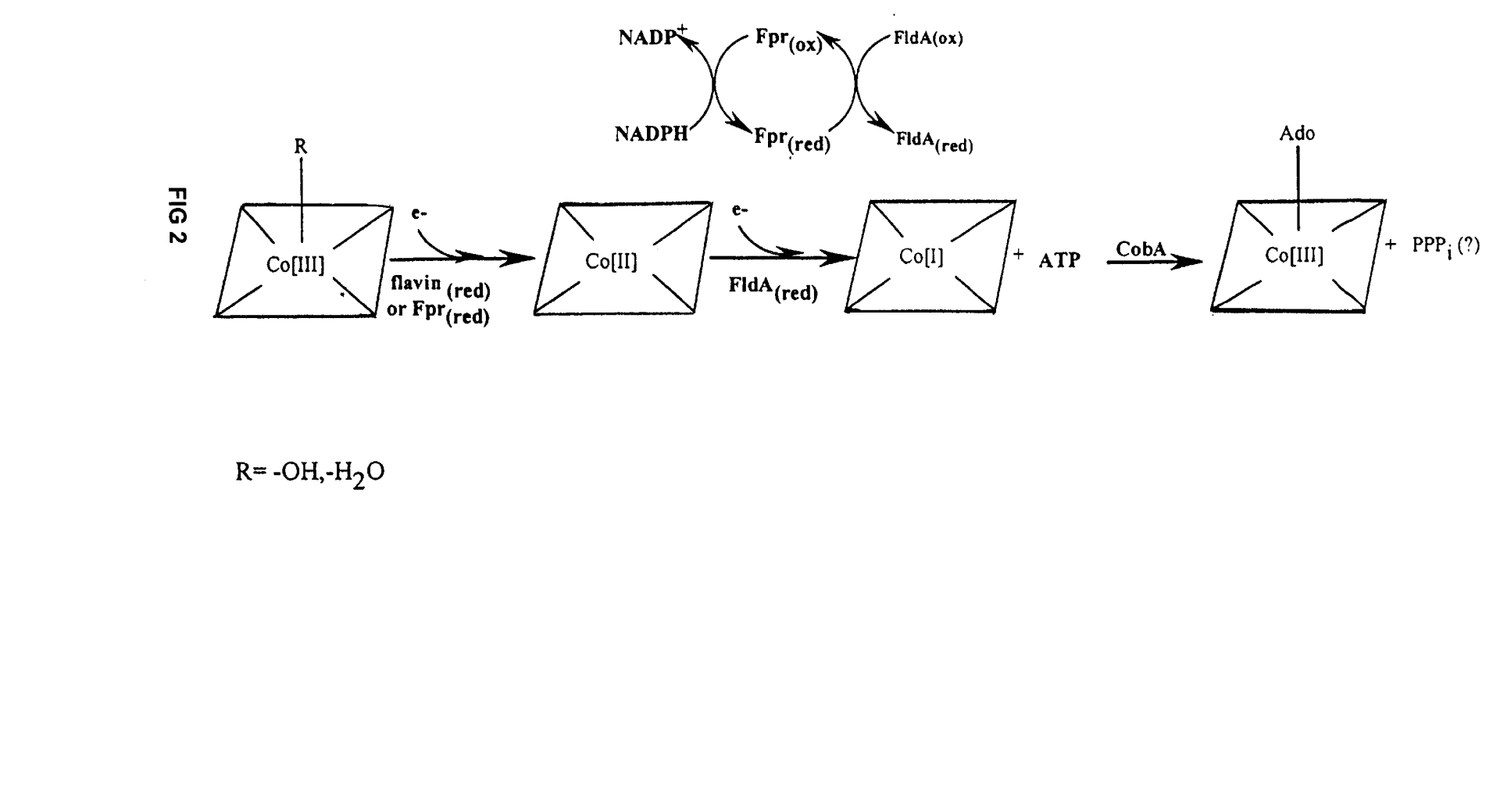
FIG. 2 illustrates the synthesis of adenosylcobalamin from cyanocobalamin.

The generation of adenosylcobalamin from non-adenosylated cobalamin is illustrated in FIG. 2. In FIG. 2, the following abbreviations are used: Ado for 5' deoxyadenosine or adenosyl; e⁻ for electron; flavin(red) for reduced forms of flavin nucleotides; NADP+ for nicotinamide adenine dinucleotide phosphate; NADPH for nicotinamide adenine dinucleotide phosphate in the reduced form; $Fpr_{(ox)}$ for oxidized Fpr enzyme; $Fpr_{(red)}$ for reduced Fpr enzyme; $Fld_{(ox)}$ for oxidized flavodoxin enzyme; $Fld_{(red)}$ for reduced flavodoxin enzyme; $PPP_i$ for tripolyphosphate (postulated as the by-product of the CobA reaction in *Salmonella typhinurium* enterica). The non-adenosylated form of cobalamin, Co[III] is reduced to Co[II] by the action of reduced flavin nucleotides or reduced Fpr. Reduced Fpr is required for generating reduced FldA.

It is the reduced form of FldA that is coupled to CobA to generate Co[I] for adenosyltransfer by CobA.

Based on this understanding of the necessary enzymes, it now becomes possible to design host bacterial stains and/or plasmids for use in reactions to remove any limitations arising from the need for adenosylcobalamin in the process. All that is required is that the bacteria have increased capability to produce the FldA, CobA and, preferably, the Fpr enzymes. All of these enzymes were previously known to the art. A gene from *Salmonella typhimurium* enterica encoding the CobA enzyme was described by Suh and Escalante-Semerena, *J. Bacteriol.* 177(4):921–925 (1995). A gene derived from *Escherichia coli* encoding the FldA enzyme is described, and its sequence presented, in Osborne et al., *J. Bacteriol.* 173(5):1729–1737 (1991). A gene, also derived from *E. coli*, encoding the Fpr enzyme is described in Bianchi et al., *J. Bacteriol.* 175(6):1590–1595 (1993). To ensure that at least one embodiment of each enzyme is enabled by this application, the DNA coding sequences for these three enzymes, CobA, FldA and Fpr are presented below as SEQ ID NO: 1, 3, and 5 below.

The knowledge that CobA and reduced FldA together can catalyze the production of adenosylcobalamin makes it possible to contemplate expression vectors for transfer into any desired microbial host in order to produce ample supplies of adenosylcobalamin in that host. Since the sequences of the genes encoding the required enzymes are known, and presented here as well, it is well within the ability of those of skill in the art of microbial expression systems to insert those coding sequences into expression vectors behind competent heterologous promoters to produce expression cassettes for the enzymes. These genes can also be inserted into a single plasmid which will express all the required enzymes in a host into which the plasmid is transferred.

It is also contemplated that the enzymes CobA and FldA, also preferably with Fpr, can be used in cell free systems to make adenosylcobalamin. As described here, these enzymes together, in the presence of NADPH and ATP, are sufficient to make adenosylcobalamin from non-adenosylated cobalamin. There may be some circumstances in which enzymatic synthesis of the molecule outside of a bacterial host may be desired, and that now becomes possible as well.

One of the difficulties in adding additional adenosylcobalamin to a microbial fermentation process, and one of the reasons the compound is relatively expensive, is that the molecule is very light sensitive. It is difficult to add it externally to a fermentation process in a way that does not also degrade quantities of the molecule. Therefore it is inherently better if the fermentation process itself can be engineered so that the adenosylcobalamin needed for the process can be produced endogenously in the fermentation reaction itself. The technique described here permits that to be done. Since a plasmid may now be constructed having the capability to express the three enzymes that are clearly sufficient to reduce and add the adenosyl group to a cobalamin molecule, bacteria which act as hosts for this plasmid are able to synthesize their own adenosylcobalamin from cyanocobalamin, and thus no longer require the addition of the relatively expensive adenosylcobalamin. The system can also allow efficient recycling of cobalamin molecules in bacterial cells.

The flavodoxin enzyme was known, in another context, to be a part of a multi-enzyme process for the reduction of the cobalt atom in the cobalamin molecule. A complex is known to exist between the methionine synthase (MetH) enzyme and flavodoxin. MetH contains cobalamin bound as a cofactor. In this complex, the cobalt atom was known to be reduced from the 2+ state to the 1+ state, as part of the reductive activation cycle of the MetH enzyme. However, there was no indication in the art anywhere that flavodoxin could accomplish a similar objective in a complex formed with the CobA enzyme, when cobalamin carrying a cobalt in the 2+ state was bound to CobA. In fact, there is every reason to believe that the mechanism of action of MetH is much different than that of the CobA enzyme. For one thing, the CobA and MetH enzymes bind to cobalamin in very different ways. In the instance of CobA, cobalamin binds a large cleft formed by two beta strands on one side of the ring of the enzyme and two alpha helices on the other side. There is also a long alpha helix on the CobA enzyme that runs below cobalamin on the lower ligand side. By contrast, when binding to MetH, cobalamin binds to an alpha helical bundle formed by the internal domain of the cobalamin binding region in MetH. The lower ligand is displaced from its normal position as a ligand to the cobalt in cobalamin and extends to fit in a pocket formed by the carboxyl terminal domain of the fragment. In short, there is no similarity whatsoever in the way that cobalamin was known to bind to CobA and the way in which cobalamin was known to bind to MetH. In addition the lower ligand is not displaced upon binding of CobA to cobalamin as it is in the binding of MetH to cobalamin. All of this indicates that whatever happens in the interaction between CobA and the cobalamin molecule, happens in a much different mechanism than that used by MetH.

Also, in the case of MetH, cobalamin is used as a cofactor, which always remains enzyme-bound. That complex is acted on by flavodoxin. In contrast, CobA uses cobalamin as a substrate thus it binds to it transiently only during the reduction-adenosylation reaction. Also, in general, the complexes formed by these enzymes are extraordinarily specific for the reactions involved.

As a result of the difficulty in producing adenosylcobalamin, cyanocobalamin and adenosylcobalamin have greatly different values, at least given the state of the art in the U.S. in the spring of the year 2000. Current market prices for cyanocobalamin are something under $50.00 US per gram while market price for adenosylcobalamin is in excess of $200.00 US per gram. This difference reflects the lack of efficient processes to produce adenosylcobalamin.

In one embodiment, what is contemplated here is a method of overproducing flavodoxin reductase, flavodoxin and CobA in a bacterial host strain intended for a fermentation process so as to confer upon that strain the ability to continually recycle cobalamin during the fermentation process. It is believed that this technique will be widely applicable to microorganism hosts which are fermented to produce proteins or other metabolites as products. There is also evidence that the active domains of the three enzymes are conserved sufficiently amongst bacterial species such that forms of these enzymes from heterologous hosts can be used in other bacterial hosts without affecting their efficacy. For example, in the examples described below, the Fpr and FldA enzymes derived from *E. coli* are used with the CobA enzyme derived from *S. enterica*. These enzymes were capable of acting together to catalyze the reduction of cobalamin to adenosylcobalamin. This demonstrates the heterologous enzymes will work for this purpose, and that the enzymes will work to produce adenosylcobalamin, even in hosts in which they are not natively found.

EXAMPLES

Overproduction of Flavodoxin (FldA) and Generation of Cell-free Extracts.

The flavodoxin enzyme was overproduced from four 2 L cultures of *E. coli* strain DH1/pDHO2 (R. G. Matthews, University of Michigan) grown on Luria Bertani broth containing 100 μg/ml of ampicillin. Cells were grown at 37° C. to an $A_{650}$ of about 0.7. Isopropyl-1-thio-β-D-galactoside (IPTG) was added to a final concentration of 400 μM, and the incubation was continued overnight. After the incubation cells were pelleted by centrifugation at 10,000×g for 10 minutes using a Sorvall GSA rotor (DuPont Instruments), cell pellets were resuspended in 20 ml of 50 mM Tris-Cl buffer pH 7.4 at 4° C. containing 16 µg of the protease inhibitor phenylmethylsufonyl fluoride (PMSF) per ml of extract. The cell suspension was broken by sonication using a Sonic Dismembrator (model 550 Fisher Scientific) for 7.5 min (small tip, setting of 3, 50% duty). Cell-free extracts were generated by centrifugation at 40,000×g for 1.5 hrs using a KOMP Spin rotor (model KA-21.50).

Overproduction of Ferredoxin(Flavodoxin): $NADP^+$ oxidoreductase (Fpr) and generation of cell-free extracts. Fpr was overproduced from strain JE4937 (E. coli C-1a/pEE1010, a gift from Elisabeth Haggard-Ljungquist, Stockholm University, Stockholm, Sweden) grown overnight on Luria Bertani broth containing 100 µg/ml of ampicillin at 37° C. Following incubation, cells were pelleted by centrifugation at 10,000×g for 10 minutes using a Sorvall GSA rotor. Cell pellets were resuspended in 50 ml of 50 mM Tris-Cl buffer pH 7.4 at 4° C. containing 16 µg/ml of PMSF. The cell suspension was broken by sonication with a large tip (setting of 6, 50% duty) for 5 min. Cell-free extracts were generated as described above.

Purification of the ATP:corrinoid adenosyltransferase (CobA) enzyme from Salmonella enterica serovar Typhimurium LT2. Purification of the CobA enzyme was performed as described in Suh and Escalante-Semerena, J. Bacteriol. 177(4):921–925 (1995), the disclosure of which is hereby incorporated by reference.

Purification of Histidine-tagged Fre enzyme. Purification of His-tag Fre enzyme was performed as described in Fonseca and Escalante-Semerena, J. Bacteriol. Reduction of Cob(III) alamin to Cob(II) alamin in Salmonella enterica serovar Tryphimurium LT2 (in press), the disclosure of which is hereby incorporated by reference.

Purification of Fpr From E. coli

Step 1. Mass culturing of the overexpressing strain and generation of cell-free extracts. Cells of the Fpr overexpressing strain were grown and harvested as described above, except 0.6% glucose was also added to the culture medium. Approximately 20.2 g of cells (16.7 g/L of wet mass), were resuspended in 50 mM Tris-Cl buffer pH 7.5 at 4° C. (buffer A) containing 16 µg/ml PMSF. The cell suspension was broken by sonication as described above for a total time of 18 minutes. Cell-free extracts were generated by centrifugation as described above.

Step 2. Ion exchange chromatography. The sample was loaded onto a (2.5×20 cm, 41.7 ml bed-volume) DEAE 650M TSK anion exchange resin (Tosohaas) equilibrated with buffer A. The column was developed at a flow rate of 60 ml $h^{-1}$. After loading the sample, the column was washed with 171 ml of the buffer A, followed by a 63 ml wash with 1 M NaCl. Purification of Fpr was monitored by SDS-PAGE. Fractions containing Fpr were pooled for further purification.

Step 3. Dye-ligand chromatography. Fpr fractions from the previous step were loaded onto a Reactive Red 120 (Sigma) column (2.5×20 cm, 76 ml bed-volume), equilibrated with buffer A. The column was developed at a flow rate of 79 ml $h^{-1}$. After washing the column with 119 ml of buffer A, bound proteins were eluted with a 316 ml linear gradient (1.0 M NaCl in buffer A). Following the gradient, the column was washed with 240 mL 1.3 M NaCl to elute tightly bound proteins. Fractions containing Fpr, as judged by SDS-PAGE and UV/visible spectrum of the enzyme-bound flavin, were pooled and concentrated using a Centriprep 10™ concentrator (Amicon, Beverly, Mass.).

Step 4. Anion exchange chromatography. The purified Fpr sample was loaded onto a Resource Q FPLC column (Pharmacia) equilibrated with buffer A. Bound proteins were eluted with a linear gradient of NaCl (1.0 M) in buffer A. Fpr was purified to about 98% homogeneity after this step as judged by SDS-PAGE.

Purification of E. coli FldA.

Step 1. Overproduction of FldA and generation of cell-free extracts. Cells of strain DH1/pDHO2 were grown and harvested as described above.

Step 2. Anion exchange chromatography #1. The cell-free extract was loaded onto a DEAE 650M (2.5×20 cm, 69.7 ml bed-volume) equilibrated with buffer A. The column was washed with 70 ml of loading buffer followed by 140 ml of 100 mM NaOAc buffer pH 5.0. Bound proteins were eluted with a linear gradient 100–500 mM. NaCl in 100 mM NaOAc buffer pH 5.0. The pH of the FldA containing fractions, as judged by their bright yellow color, was brought up to 7.0 with 2M Tris-Cl buffer pH 8.0 at 4° C. Fractions containing the FldA protein were pooled and dialyzed against buffer A.

Step 3. Anion exchange chromatography #2. The dialyzed sample was loaded onto a POROS HQ (PE Biosystems) anion exchange FPLC column (1.6×3.5 cm, 7.0 ml bed-volume) column equilibrated with buffer A. The column was washed with 14 ml of buffer A followed by a linear gradient of 0-1.5 M NaCl in buffer A.

Fractions containing 95% homogenous FldA were pooled, dialyzed against buffer A and stored at −90° C. in buffer A+20% glycerol.

In vitro Activity Assays

Corrinoid adenosylation assays. ATP:corrinoid adenosyltransferase (CobA) assays were performed as described Suh and Escalante-Semerena, J. Bacteriol. 177(4):921–925 (1995), except the $MnCl_2$ concentration was increased to 1.6 µmol and the ATP concentration was increased to 1.0 µmol.

Enzymic reduction of cob(III)alamin to cob(I)alamin coupled to adenosyltransfer. The assay is a modification of the corrinoid adenosylation assay reported by Suh and Escalante-Semerena, J. Bacteriol., 177(4):921–925 (1995). Conversion of HO-cob(III)alamin (HOCbl) to adenosylcobalamin (AdoCbl) was monitored spectrophotometrically by looking at changes in the UV/visible spectrum of the corrinoid substrate before the reaction was started, during incubation and at the end-point of the assay. The assays contained in a final volume of 1 ml: HO-cob(III)alamin, (50 nmol), nicotinamide adenine dinucleotide phosphate (NADPH, 500 nmol), flavin mononucleotide (FMN, 50 nmol), purified His-tag Fre enzyme (4.8 µg), Fpr cell-free extract (100–200 µl), FldA cell-free extract (100 µl), purified CobA enzyme (32.5 µg), ATP and $MnCl_2$ as above. The reaction mixture was incubated at 37° C. in a Perkin Elmer Lambda 6 spectrophotometer. UV/visible spectra of the reaction mixture were recorded approximately every 30 min after the reaction was started until conversion to AdoCbl was deemed complete. In later assays, the Fpr enzyme was also used to carry out the reduction of cob(III) alamin to cob(II) alamin, and thus, FMN and Fre were omitted from these assays.

Cytochrome c reductase assays. Enzymic activity of the Fpr enzyme was monitored using the cytochrome c reductase assay as reported by Fujii and Huennekens, J. Biol. Chem. 249(21):6745–6753 (1974), except the assays were performed under anoxic conditions to mimic conditions used in coupled corrinoid adenosylation assays.

Figure 3:
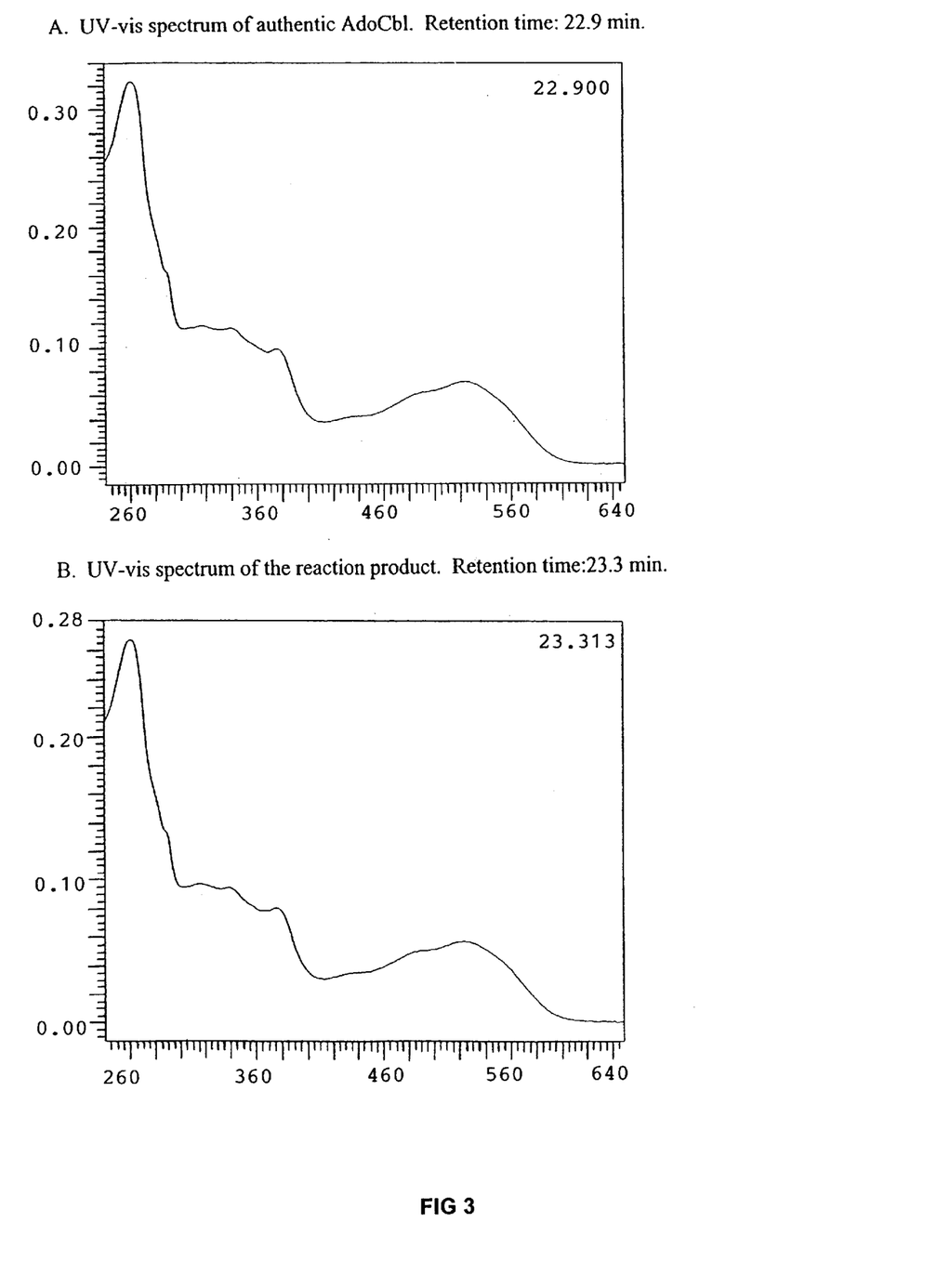
FIG. 3 contains a graphical representation of some of the data from one of the examples below.

HPLC analysis of reaction products. The products of the corrinoid adenosylation assays were analyzed by Reverse Phase chromatography on a Prodigy ODS(8) column (Phenomenex) attached to a Waters HPLC system as described by O'Toole et al. supra. A photodiode array detector (Waters) was used to identify corrinoids by their UV/vis spectra. Authentic HOCbl and AdoCbl were used as standards. The UV/vis spectra output traces of authentic AdoCbl and the reaction product isolated using this procedure are compared in FIG. 3.

The results shown herein demonstrate that a defined in vitro reducing system can be used to generate adenosylcobalamin from non-adenosylated cobalamin. The results strongly suggest that this system can be applied in vivo for efficient generation and recycling of adenosylcobalamin in bacterial cells as well for the in vitro synthesis of adenosylcobalamin.

We claim:

1. A method of producing adenosylcobalamin comprising the steps of
providing non-adenosylated cobalamin in which the cobalt atom has been reduced to a 2+ state;
exposing the non-adenosylated cobalamin to the bacterial enzymes ATP:corrinoid adenosyltransferase (CobA), flavodoxin (FldA), and flavodoxin reductase (Fpr) in the presence of ATP under conditions suitable for the production of adenosylcobalamin, wherein the CobA and FldA enzymes are not natively from the same host organism; and
detecting adenosylcobalamin produced by the reaction.

2. A method as claimed in claim 1 where in the exposing step is performed in vivo in a microbial host.

3. A method as claimed in claim 1 wherein the enzyme ATP:corrinoid adenosyltransferase (CobA) is from Salmonella typhimurium.

4. A method as claimed in claim 1 wherein the flavodoxin (FldA) enzyme is from *Escherichia coli*.

5. A method of producing adenosylcobalamin comprising the steps of
providing non-adenosylated cobalamin in which the cobalt atom has been reduced to a 2+ state;
exposing the non-adenosylated cobalamin to the enzymes ATP:corrinoid adenosyltransferase (CobA) from Salmonella typhimurium, flavodoxin (FldA) from *Escherichia coli*, and flavodoxin reductase from *Escherichia coli* in the presence of ATP under conditions suitable for the production of adenosylcobalamin; and
detecting adenosylcobalamin produced by the reaction.

6. A method of producing adenosylcobalamin comprising the steps of
providing non-adenosylated cobalamin in which the cobalt atom has been reduced to a 2+ state; and
exposing in vitro the non-adenosylated cobalamin to the bacterial enzymes ATP:corrinoid adenosyltransferase (CobA) from *Salmonella typhimurium*, flavodoxin (FldA) from *Escherichia coli*, and flavodoxin reductase from *Escherichia coli* in the presence of ATP under conditions suitable for the production of adenosylcobalamin.

* * * * *